United States Patent [19]
Dahms

[11] Patent Number: 5,453,377
[45] Date of Patent: Sep. 26, 1995

[54] METHODS FOR MAKING IODINE-FREE KARL FISCHER REAGENTS

[76] Inventor: Harald Dahms, 472 Madison Ave., Toms River, N.J. 08753

[21] Appl. No.: 263,039

[22] Filed: Jun. 21, 1994

Related U.S. Application Data

[63] Continuation-in-part of Ser. No. 97,110, Jul. 26, 1993, Pat. No. 5,389,545.

[51] Int. Cl.⁶ .......................... G01N 33/00; G01N 33/18
[52] U.S. Cl. .................. 436/8; 436/39; 436/42; 422/61; 252/408.1
[58] Field of Search .................. 436/8, 39, 42, 436/163, 111, 122, 125; 422/61; 252/408.1

[56] References Cited

U.S. PATENT DOCUMENTS

| | | | |
|---|---|---|---|
| 2,780,601 | 2/1957 | Blomgren | 252/408.1 |
| 2,967,155 | 1/1961 | Blomgren et al. | 252/408 |
| 4,351,744 | 9/1982 | Muroi et al. | 252/408.1 |
| 4,378,972 | 4/1983 | Scholz | 436/42 |
| 4,725,552 | 2/1988 | Dahms | 436/42 |
| 4,740,471 | 4/1988 | Scholz | 436/42 |
| 4,802,957 | 2/1989 | Kuwatz et al. | 204/1 T |
| 5,102,804 | 4/1992 | Fischer et al. | 436/42 |
| 5,139,955 | 8/1992 | Scholz | 436/42 |
| 5,389,545 | 2/1995 | Dahms | 436/42 |

FOREIGN PATENT DOCUMENTS 2234066  1/1991  United Kingdom .

*Primary Examiner*—Robert J. Warden
*Assistant Examiner*—N. Bhat

[57] ABSTRACT

Various methods are described for producing volumetric one-component iodine-free Karl Fischer reagents useful for determining the water content of a sample, the reagents containing triiodide as the dominant oxidizing species. The reagents contain a reducing agent such as $SO_2$, a buffer such as amine, a solvent, and an oxidizing agent that is triiodide, generally in the form of triiodide ions. The molar amount of $SO_2$ in these reagents is greater than the molar amount of triiodide. The characteristics of these methods generally include the formation of triiodide in a first solution having a first amine/$SO_2$ ratio prior to obtaining a final solution having the final amine/$SO_2$ ratio. These methods provide economies in the ingredients used, and yield reagents exhibiting good liter strength and enhanced reproducibility of properties from one production run to the next.

28 Claims, No Drawings

METHODS FOR MAKING IODINE-FREE KARL FISCHER REAGENTS

CROSS REFERENCE TO RELATED APPLICATION

This application is a continuation-in-part of application Ser. No. 08/097,110 filed Jul. 26, 1993 now U.S. Pat. No. 5,389,545.

DESCRIPTION

1. Field of the Invention

This invention relates to methods for making one-component reagents for water determination using the Karl Fischer reaction, and more particularly to methods for making volumetric one-component, pyridine-free reagents which are iodine-free and contain triiodide as an oxidizing agent, a reducing agent such as $SO_2$, a buffer such as an amine, and a solvent.

2. Background Art

The determination of moisture in materials such as liquids and solids by the Karl Fischer reaction is well known and widely used since it was first described by Karl Fischer in Angewandte Chemie 48, pages 394–396 (1935). Numerous publications have also described this technique for water determination, and reference is made to a general text by J. Mitchell, Jr. and D. M. Smith, entitled "Aquametry", published by John Wiley and Sons, 1980. Reference is also made to a publication by E. Scholz entitled "Karl Fischer Titration", published by Springer Verlag in 1984.

In a Karl Fischer reaction, the water to be determined reacts with iodine on a quantitative basis and, consequently, the amount of reacted iodine is a measure of the amount of water present in the sample. The reaction proceeds according to the following expression:

(1) 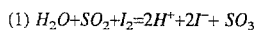

$$H_2O + SO_2 + I_2 = 2H^+ + 2I^- + SO_3$$

KF reagents are used in several types of analysis. A volumetric analysis using a volumetric reagent determines moisture by measuring tile volume of the Karl Fischer reagent consumed during the analysis. A coulometric analysis using a coulometric reagent generates iodine by passing a current through the reagent and determines the moisture from the amount of current.

Volumetric Karl Fischer reagents are divided into two groups, one-component and two-component systems. In the one-component systems, all ingredients (iodine, buffer, $SO_2$ and solvent) are in one solution. In the two-component systems, the "vessel" solution contains the buffer, $SO_2$, and a solvent, while the "titrant" solution contains iodine in a suitable solvent. Many differences exist between one component and two component reagents, and the teachings with respect to each cannot be directly applied to the other.

Both types of systems, one-component and two-component, have their advantages. The one-component reagents are more economical for users because they have to buy only one solution. However, there are disadvantages, particularly with respect to stability and shelf life. As soon as iodine, $SO_2$ and amine buffers are combined in the same solution they slowly react with each other. This reaction decreases the iodine level and therefore reduces the tiler strength. This in turn limits the stability and shelf life of the reagent. This complication (which does not exist in two-component reagents) requires that the type of amine and the ratio of amine to $SO_2$ have to be carefully controlled to furnish good one-component reagents. This stability problem has been recognized by Blomgren et al in U.S. Pat. Nos. 2,780,601. and 2,967,155, both of which describe pyridine based reagents. In the former, a suitable concentration of iodide ions was added as a stabilizing agent to reduce the speed of the spontaneous titer decrease so that the titer of the reagent will be less affected by the aforementioned spontaneous side reactions. However, it was found that the problem persisted even in the reagents containing iodide ions as stabilizing agents. Therefore, the invention of U.S. Pat. No. 2,967,155 was directed to the use of a stabilizing base in the reagent, where the base strength of the stabilizing additive was chosen to be greater than that of the accelerating base (pyridine) used in these reagents. Generally, the use of pyridine is to be avoided due to odor and health problems, as well as its inferior performance characteristics.

U.S. Pat. No. 5,102,804 describes a modified Karl Fischer reagent for the determination of water which contains another oxidizing source instead of iodine. This source is an iodine halide or a mixture of halide and salt of an aromatic nitrogen containing heterocyclic corn pound. Advantages are stated to be that of increased stability and quicker reaction times.

U.S. Pat. Nos. 4,378,972 and 4,740,471 describe Karl Fischer reagents consisting of iodine, $SO_2$ and amines. UK patent application GB 2 234 066A describes a two-component reagent in which the titrant can include triiodide.

While the prior art has provided some solutions to the problem of shelf life in one-component Karl Fischer reactions, it is desirable to provide one-component volumetric reagents which exhibit high titer strength and improved accuracy in addition to enhanced shelf life. This has been accomplished in the present invention wherein iodine-free volumetric one-component reagents are described where the oxidizing species is triiodide that is present in the reagent as the triiodide ion $I_3^-$ or undissociated triiodide species.

In the course of Applicant's experiments it was discovered that methods for making one-component iodine-free reagents in which all of the triiodide was not formed prior to establishing the final amine/$SO_2$ ratio in the final reagent mixture often produced reagents that were inferior to reagents made by the inventive methods to be described hereinafter. It was also found that the aforementioned inferior methods for making these reagents have other disadvantages in comparison to the inventive methods herein. Some of these disadvantages include the following:

1. More iodine is required than would be theoretically expected to yield a reagent having a given titer strength.

2. When multiple batches of reagent are made using these disadvantageous methods, the reproducibility from batch to batch is not good. This lack of reproducibility is a significant factor in commercial production requirements.

Accordingly, it is a primary object of this invention to provide advantageous methods for making volumetric one-component, iodine-free Karl Fischer reagents.

It is another object of this invention to provide an iodine-free or one-component volumetric reagent for the Karl Fischer determination of water content, where the dominant oxidizing species is triiodide.

It is another object of this invention to provide an improved pyridine-free, iodine-free one-component volumetric reagent, methods For making this reagent, and a method For using this reagent to determine water content, wherein improved accuracy results.

It is another object of this invention to provide improved methods for making iodine-free one-component volumetric Karl Fischer reagents containing triiodide, a reducing agent such as $SO_2$, a buffer, and a solvent wherein any iodine present in said reagents is present in an amount less than 1% of the amount of triiodide.

It is another object of this invention to provide inexpensive methods for making iodine-free one-component Karl Fischer reagents, where the methods provide reagents whose properties are reproducible over many production runs.

It is another object of this invention to provide a process for water determination using the methods and reagents described in the preceding objects.

BRIEF SUMMARY OF THE INVENTION

This invention relates to methods for making improved one-component volumetric reagents for use in determining the water content of a sample using the Karl Fischer reaction. These new reagents are pyridine-free, and iodine-free and contain triiodide (present in the reagent as triiodide ions $I_3^-$ undissociated triiodide species) as an oxidizing agent, a reducing agent such as $SO_2$, a buffer such as an amine to maintain a constant pH, and a suitable solvent. The molar amount of the reducing agent (such as $SO_2$) is greater than the molar amount of triiodide in these new reagents. In these reagents, the dominant oxidizing agent is triiodide, and any iodine which may be present is present in an amount less than 1% of the amount of triiodide. As used herein, the term "iodine-free" means that there is no iodine in these reagents or, if iodine is present, it is present in only trace amounts, i.e., less than 0.01 moles per liter.

In one preferred embodiment of this invention, all of the triiodide is formed in a first solution (that optimally can contain a fraction of the final amine and/or $SO_2$ content) prior to establishing the final amine/$SO_2$ ratio. The first solution is iodine-free or essentially iodine-free, and the triiodide is preferably formed from iodine by reaction with water via the Karl Fischer reaction. After this, the final amine/$SO_2$ ratio is established by adding amine and/or $SO_2$ to produce a second solution (reagent) in which the molar amount of $SO_2$ is greater than the molar amount of triiodide, and in which the triiodide concentration is preferably in the range of about 0.05–0.6 moles per liter.

By following this procedure, the amount of iodine (or iodide) that is used to make a reagent having a fixed titer is less than that needed using methods of preparation in which the triiodide is not formed prior to establishing the final amine/$SO_2$ mixture. This iodine saving feature becomes significant as the number of production runs increases in view of the expensive nature of iodine.

Another advantage of the methods of this embodiment is that the quality and uniformity of the reagents from batch to batch when made by these inventive methods are better than those made by a method in which the triiodide is not formed prior to establishing the final amine/$SO_2$ mixture. This good reproducibility is also a production advantage.

In another embodiment, amine and $SO_2$ are present in (a first solution) containing a small amount of water. The amount of water in molar terms is greater than the total amount (in molar terms) of the iodine to be added. A solid source (such as a powder) of iodine is then placed in this solution. At the moment it dissolves it is converted to iodide ions $I^-$ and all of the water is consumed. As more iodine is dissolved, it immediately combines with the iodide ions to form triiodide. In this process iodine is never dissolved in the solution in an amount 0.01 moles or greater. Thus, even though no further amounts of amine and $SO_2$ need to be added, the problems mentioned above are avoided, and the final one-component reagent is iodine-free.

As an alternative to using water to convert iodine to triiodide in the formation of iodine-free one-component Karl Fischer reagents, heat can be applied for a limited time to a solution containing an amine, $SO_2$ and iodine and having a desired amine/$SO_2$ ratio. In this embodiment, however, it may be that not all of the triiodide is formed in the solution prior to establishing the final amine/$SO_2$ ratio.

In use, a known amount of this reagent is added to a reaction cell containing a solvent in order to titrate to a first endpoint (thereby removing any water from the solvent). The sample is then dissolved in the solvent and the reagent is again added, to have titration to the same endpoint. The endpoints are typically indicated visually or through electronic circuitry. Since the titer of the reagent had been previously determined by means of a known quantity of water and since the volume of the added reagent is known, the water content of the sample can be calculated.

These and other objects, features, and advantages will be apparent from the following more particular description of the preferred embodiments.

DETAILED DESCRIPTION OF THE PREFERRED EMBODIMENTS

The reagents of this invention are pyridine-free one-component volumetric reagents that are iodine-free and contain triiodide as an oxidizing agent. The reagents also contain a reducing agent such as $SO_2$, a buffer such as an amine, and a solvent.

In addition to the basic Karl Fischer reaction described above as equation 1, it is known that iodide ions can be added to a Karl Fischer reagent containing $SO_2$, a buffer such as an amine, and a solvent by adding water to the Karl Fischer reagent. The iodide ions combine with iodine according to the following expression:

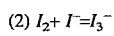
(2) $I_2 + I^- = I_3^-$

The species $I_3^-$ is the triiodide ion. Reaction 2 can occur in aqueous and in alcoholic solutions, as well as in other solutions.

The reaction given by Equation 2 can be used in certain, special ways to make the improved one-component reagents of this invention since the reaction is driven predominantly to the right hand side of the equation, i.e., to $I_3^-$. The methods of this invention using equations (1) and (2) establish a first solution having a first amine/$SO_2$ ratio and then establish a second solution that's iodine-free and contains triiodide, the second solution having an amine/$SO_2$ ratio that is different than the first amine/$SO_2$ ratio. Following these general guidelines provides the advantages listed hereinabove.

Several different methods can be employed to achieve the general guidelines of the previous paragraph. Four such approaches are the following:

METHOD I

A first solution is made containing a solvent in which the desired final amount of amine is present. Slightly more than ⅓ of what will be the total addition of iodine is then added to this solution. After this, water is added in a sufficient amount to convert the iodine to iodide when $SO_2$ is later added. At this time, $SO_2$ is slowly added in an amount just enough to convert all of the iodine to iodide. This point in the process is easily noticed since the solution will turn from a brown color (indicative of iodine) to a clear solution (indicative of iodide). Then the balance of the iodine is added to the solution, all of the iodine being converted to triiodide due to reactions given by equations 1 and 2. As a final step, $SO_2$ is bubbled into the solution in an amount necessary to provide a second solution (reagent) having the desired final amine/$SO_2$ ratio.

METHOD 2

The desired final amount of $SO_2$ is dissolved in a suitable solvent to which is added a small amount of amine (preferably less than 0.3 times the amount of $SO_2$, in molar terms) to produce a first solution. After this iodine is added to this solution in an amount that is slightly more than ⅓ the total amount of iodine that will be added to the solution. Water is then slowly added to the solution in the amount needed to convert the iodine to iodide in accordance with equation 1 above. This will be evidenced by the changing of color of the solution from brown (indicative of iodine) to colorless (indicative of iodide). After this, more iodine is added. The amount of the added iodine is the balance of the total amount required to produce the desired amount of triiodide. The balance of the amine needed for the finished product is then added to produce a second solution (reagent), the amount of amine being added being the amount necessary to have the desired, final amine/$SO_2$ ratio.

In methods 1 and 2, there were no additional amounts of either amine (method 1) or $SO_2$ (method 2) added after the start of the process. It will be appreciated, however, that both amine and $SO_2$ can be present at the start of the process, in amounts that do not yield the desired final amine/$SO_2$ ratio.

When weak amines (those that are not strongly basic) such as imidazole and its derivatives are used, the first solution has an amine/$SO_2$ ratio outside the range 0.4/1–8/1. The second solution (the final one-component Karl Fischer reagent) is prepared by adjusting the relative amounts of amine and $SO_2$ to have a desired final amine/$SO_2$ ratio within the range of about 0.3/1–12/1.

When strong amines (those that are strongly basic) such as primary and secondary acyclic amines are used, the first solution is prepared to have an amine/$SO_2$ ratio outside the range 0.6/1–1.2/1. The second solution (the one-component Karl Fischer reagent) is prepared by adjusting the relative amounts of amine and $SO_2$ to have a desired final amine/$SO_2$ ratio within the range of about 0.4/1–1.5/1.

METHOD 3

Iodine and iodide (such as an iodide salt) are mixed in a solvent to form triiodide, the solution being iodine-free. The final $SO_2$ and amine concentrations are then established by adding these ingredients or by adding another solution containing amine and $SO_2$ in tile desired final amine/$SO_2$ ratio. This method may be the least preferred because it requires the use of iodide as an initial ingredient and the iodide is expensive.

METHOD 4

This method starts with a solution containing a solvent, an amine, a reducing agent such as $SO_2$ and water. Iodine is then added but is converted into triiodide before it can dissolve in the solution. Thus, at no time will there be iodine dissolved in the solution in amounts equal to or greater than 0.01 mole.

The following examples 1, 3, 5, 9 and 10 illustrate tile aforementioned methods in accordance with the present invention, while examples 2, 4 and 6 illustrate the inferior results that are obtained when the necessary triiodide concentration is not formed prior to establishing the final amine/$SO_2$ ratio.

Examples 7 and 8 illustrate the variations that can result when different amines are used.

EXAMPLE 1

This example illustrates Method 1, above.

2 moles of imidazole are dissolved in 1 liter of ethylene glycolmononmethylether. Now 0.2 mole of iodine is also dissolved. 0.1 mole of water is added. Now, 0.25 mole of $SO_2$ is bubbled into the solution. This results in a solution having only 0.15 moles of $SO_2$ since the $SO_2$ reacts with the iodine and water. Small amounts of water are then added until the brown solution turns clear, indicating that all iodine has been converted to 0.4 mole of iodide. Then 0.35 mole of iodine is added to the solution, and is converted to triiodide by reaction with the 0.4 moles of iodide present in the solution. Finally, 1.6 more moles of $SO_2$ are added while cooling the solution.

This solution was tested in a commercial titration apparatus and performed very well.

EXAMPLE 2

This example illustrates a method wherein the triiodide is not formed prior to establishing the desired, final amine/$SO_2$ ratio.

The process of Example 1 was repeated with the same ingredients and the same amounts of ingredients, except that the sequence of adding the ingredients was changed to the following:

dissolve all the imidazole dissolve all the sulfur dioxide dissolve all the iodine add all the water While it would be expected that the reagents made by the methods of examples 1 and 2 would be similar, it turns out that they were not. The titer strength of the reagent in Example 2 was lower than that of the reagent of Example 1. Also, by repeating the methods of examples 1 and 2 several times it was found that reagents made by the method of Example 1 were more consistent than those made by the method of Example 2, with regard to performance and titer strength. The inferior results obtained using the method of example 2 clearly demonstrate the superiority of the method of example 1.

EXAMPLE 3

This example illustrates Method 2, above.

2 moles of $SO_2$ were dissolved in 1 liter of ethyleneglycolmonomethylether. 0.3 moles imidazole and 0.5 moles diethanolamine were then dissolved.

Now, 0.2 moles of iodine were added and dissolved by stirring. Water was then added slowly until the solution turned from brown to clear, indicating that all iodine was converted to 0.4 mole of iodide. Now, 0.35 mole of iodine was added and dissolved by stirring, thereby converting all iodine to triiodide. Then 1.4 moles of imidazole was added to make the finished reagent.

The reagent was tested in a Karl Fischer water determi-

EXAMPLE 4

This example illustrates a method in which the triiodide is not formed prior to establishing the desired, final amine/$SO_2$ ratio.

The experiment of Example 3 was repeated, using the same amounts of ingredients except that they were added in the following sequence: all imidazole and diethanolamine, all sulfur dioxide, all iodine, all water. The titer of this reagent was lower than that of the reagents made using the methods of Example 3, thereby demonstrating the superiority of the method of example 3.

EXAMPLE 5

This example also illustrates Method 2, above. Here, the method of preparation in example 3 was repeated, except that in the last step instead of 1.4 moles imidazole, 1.4 moles of diethanolamine were added to make the finished reagent.

The reagent exhibited good liter strength when tested in a Karl Fischer water determination; it also yielded good results.

EXAMPLE 6

This example illustrates a variation of the method of example 5 in which the triiodide is not formed prior to establishing the desired, final amine/$SO_2$ ratio.

The method of preparation in example 5 was repeated, using the same ingredients in the same amounts, except that the ingredients were added in the sequence indicated in example 4. The titer of the reagent of example 6 was lower than that of example 5. This demonstrates the superiority of the method of example 5.

EXAMPLE 7

This example indicates the need for some variation when strongly basic amines are used.

Here, it was attempted to repeat the method of preparation in example 1 using diethanolamine instead of imidazole. A useful reagent could not be made this way because when all of the iodine was added to the diethanolamine solution the solution lost most of its brown color, thereby indicating that the iodine was lost in side reactions.

Example 7 shows that not all possible sequences are successful.

It should also be mentioned that a possible but less preferred way of making these triiodide reagents is to dissolve iodine, add more than an equimolar amount of an iodide such as sodium iodide, and then add sulfur dioxide and amine in amounts which yield the desired, final amine/$SO_2$ ratio.

EXAMPLE 8

This example is a variation of example 5, and also illustrates a suitable sequence of steps in accordance with Method 2, above.

Here, example 5 is repeated except that instead of initially dissolving 0.3 mole imidazole and 0.5 mole diethanolamine, 0.8 mole diethanolamine is dissolved (i.e., no imidazole is used).

EXAMPLE 9

This example illustrates Method 3, above.

0.4 mole iodine and 0.45 mole of an iodide salt (such as NaI) are dissolved in a solvent, such as ethyleneglycolmonomethylether, to produce triiodide and a possible excess (0.05 m) of iodide salt. Then 2 moles of imidazole are added, and 2 moles of $SO_2$ are bubbled in to produce the reagent having the desired, final amine/$SO_2$ ratio.

EXAMPLE 10

Another preferred method is to first establish a mixture of the amine, sulfur dioxide and water in the solvent and then to add the iodine afterwards. The sequence in which these first three ingredients are added does not matter. The important .feature is that they are all present before the iodine is added. In this way the iodine is converted to triiodide before it can dissolve in the solution. The following example illustrates this preferred method.

2 moles of imidazole and 0.19 mole of water were dissolved in one liter of ethyleneglycolmonomethylether. After this, 1.5 moles of sulfur dioxide were dissolved in the solution. Then 0.445 mole of iodine was dissolved by stirring. This results in a final solution containing 0.255 mole of triiodide, 0.125 mole of iodide and essentially no iodine.

For all of these examples the usual laboratory practices were followed, such as the exclusion of atmospheric moisture.

Laboratory experiments have led to the discovery that water is not needed to convert an iodine containing one-component solution to an iodine-free triiodide one-component Karl Fischer reagent. A preferred method for doing this is to expose the iodine reagent for a certain time to elevated temperatures. The elevated temperature is in the range from about 40° C. to the boiling point of the solvent. The time period required for complete conversion to triiodide will decrease as the temperature increases and may be as short as about one minute at temperatures close to the boiling point of the solvent. At a temperature of about 100° C., complete conversion will occur in less than about one hour. The elevated temperature may be applied to the finished product (i.e., the solution containing $SO_2$, amine and iodine) or during preparation of the solution. The chemical reaction that occurs to effect this transformation (iodine to triiodide) is unknown. For example, if a solution containing 2 moles of imidazole, 2 moles of sulfur dioxide and 0.5 mole of iodine in one liter of ethyleneglycolmonomethylether is exposed to a temperature of 75° C. for a period of 24 hours the solution will be converted to an iodine-free solution containing mostly triiodide as the oxidizing species. While in this example a time period of 24 hours was used, complete conversion may have occurred significantly prior to the end of the 24 hour period. This temperature treatment is widely applicable to solutions with the different amines mentioned in this specification.

This reagent was tested in a Karl Fischer water determination and yielded good results.

Application of Reagents

The reagents prepared in examples 1, 3, 5, 9 and 10 (as well as those prepared by using heat to convert iodine to triiodide) were used as volumetric reagents in a commercial titration apparatus (Ericsen Instruments Corp. Cat. No. AQ100). Each moisture analysis used 50 ml of methanol in the titration vessel. The methanol was pretitrated to a first endpoint. Then 50 mgs. of water were added to the vessel and a second titration undertaken to an identical endpoint. Accurate reproducible results were obtained.

The Karl Fischer reaction given by Equation 1 and the reaction given by Equation 2 will occur in the preparation of these reagents by methods 1, 2 and 4. This will convert iodine into triiodide so that the finished solutions are iodine-free, the oxidizing agent being triiodide. The reagent may also contain a possible excess of $I^-$.

As soon as the ratio of iodine/iodide is equal to 1, practically all of the oxidizing species becomes $I_3^-$ (triiodide) because of the reaction in Equation 2. The best results are obtained as soon as the iodide amount is at least equal to the iodine amount, i.e., $I^-/I_2 \geq 1$. If this is so, the resulting solution will be iodine-free.

As the iodide concentration is further increased, at a constant iodine concentration, it has been found that the best results are obtained when the iodide/iodine ratio is in the range of about 1–2.5. However, superior reagents are still obtained when this ratio is above 2.5.

It is recognized that some presently used Karl Fischer reagents of the single component type may contain limited amounts of triiodide in addition to some iodide. This occurs because solvents may contain small amounts of water. Due to this, the reactions given in Equations 1 and 2 may occur to a limited extent and therefore presently used reagents may contain some triiodide in addition to iodine. The relative amounts of triiodide and iodine in those prior art reagents are significantly different than those in the improved one component reagents of the present invention, however.

Several electrochemical experiments have been conducted to show that the KF reagents of this invention contain essentially only triiodide and no iodine. These experiments involved the measurement of the oxidation-reduction potential of the reagents. A platinum wire was inserted into the solutions and its voltage was measured against a reference cell. The solution contained a known amount of iodine but no iodide. Then iodide was added in known amounts while the voltage was measured. At the point where the amount of iodide added was equal to the amount of iodine ($I_2-I^-=I_3^-$) the redox potential of the platinum wire dropped suddenly by about 200 millivolt. These results prove to an electrochemist skilled in the art that triiodide was formed because the voltage drop occurred at an iodine to iodide ratio of 1. The large size of the drop (200 millivolts) shows that the amount of iodine left after the reaction is much less than 1% of the original amount of iodine.

As noted, very small amounts of iodine possibly may be present in the reagents of this invention, as is apparent from a review of Equation 2. If present, the amount of iodine will be so small that the iodine is immaterial as a titration agent. The equilibrium constant K of Equation 2 is given by the following expression:

$$K = \frac{I_3^-}{I_2} I^- \qquad (3)$$

Typically, K is in the order of $10^4$–$10^6$(moles$^{-1}$liter) in these new KF reagents and at a minimum is at least $10^3$(moles$^{-1}$liter). It can be easily shown that under these conditions there is very little iodine present as soon as more iodide than iodine is added to the reagent. For example, if 1 mole iodine per liter is combined with 1.01 moles of iodide per liter, 1 mole of triiodide is formed and 0.01 mole of iodide is left over. Even if a low K of $10^4$ is assumed, when these number are put into Equation 3 it yields $I_2 = 10^{-2}$ moles per liter. In this example, worst case assumptions were made, i.e., $K=10^4$ and $I^-=0.01$. In the more realistic case where $K=10^5$, even for $I^-=0.01$, $I_2$ is present in an amount $10^{-3}$ moles per liter.

These iodine concentrations of 0.01 and 0.001 moles per liter, respectively, are so low that they are far outside the range of present conventional single component volumetric reagents in which iodine is in the range of 0.05–0.33 moles per liter. As noted previously, "iodine-free" as used herein means an iodine concentration less than 0.01 moles per liter. A reagent using iodine as the sole oxidizing species, where the iodine concentration is less than 0.01 moles per liter, cannot be used commercially because of its extremely low titer strength. When exposed to small amounts of atmospheric moisture any such reagent would rapidly lose all its titer strength and therefore would be useless.

For commercial and technical reasons these new reagents contain triiodide in a most preferred range of 0.05–0.33 moles of triiodide per liter. However, since the new reagents can also be prepared somewhat stronger, a preferred triiodide range is 0.05–0.6 moles of triiodide per liter.

The buffers used in these new reagents are non-pyridine buffers and preferably are numerous types of amines. It has been found that imidazole and its derivatives give the best results. These derivatives are compounds that contain the imidazole ring and wherein the hydrogen of the imidazole is substituted by one or more aliphatic or aromatic groups. Good results have also been obtained with diethanolamine or other aliphatic amines such as diethylamine—in general, aliphatic amines can be used.

Suitable amine buffers, besides the most preferred imidazole, include acyclic primary, secondary, or tertiary amines optionally containing zero to three oxygen atoms. Examples include aliphatic amines such as diethanolamine, ethanolamine, triethanolamine, diethylamine, triethylamine, diisopropylamine, tri-n-butylamine, ethylenediamine, guanidine and the like. Mixtures of such amines can also be used. In addition to the above-mentioned types of amines, other suitable amines include dimethylanlline, diphenylamine and other equivalent amines. Diethanolamine is a preferred amine. Other amines known in the art can also be used.

The desired final range of the amine:$SO_2$ ratio in the triiodide reagents of this invention depends on the kind of amine used. For weak amines such as imidazole, a preferred range is 0.4/1–8/1 and up to about 0.2/1–12/1. For strong amines such as the aliphatic amines (e.g., diethanolamine), a preferred range is 0.4/1–1.5/1 and up to about 0.3/1–1.6/1.

The solvents used for these improved reagents can be chosen from those customarily used. For example, an anhydrous low molecular weight alcohol can be used, such as ethylene glycol-monomethyl ether. Other suitable solvents include alcohols having from 2–6 carbon atoms and other solvents currently used in the art to make one-component reagents.

By far the most preferred reducing agent is $SO_2$. Other reducing agents are described by Delmonte in U.S. Pat. No. 3,656,907. An example is dimethylsulfoxide. $SO_2$ may alternatively be used in an admixture with an acid such as an oxalic, sulfuric, hydroiodic, or hydrochloric acid.

In practice, these improved pyridine-free, iodine-free one-component volumetric reagents are used in the same manner as are other one-component reagents. That is, tile reagent is added in measured amounts to titrate to an endpoint identical to the beginning endpoint.

The improved reagents of this invention have surprisingly shown increased accuracy in comparison to reagents wherein the titration agent is iodine. A comparison experiment was carried out to compare the performance of the triiodide titration reagents of this invention with that of a conventional iodine reagent (made by dissolving 136 grams of imidazole in one liter of ethylene glycol monomethyl ether, followed by the dissolution of 96 grams of $SO_2$, and then the addition of 113 grams of iodine). Both solutions were used as titrants in a manual conventional titration apparatus to titrate a known amount of 50 milligrams of water in methanol. Ten titrations were performed with each solution, the accuracy being found as follows:

New reagent: 50 mg± .9 mg. Accuracy .8%.

Old reagent: 50 mg± .1 mg. Accuracy .2%.

Other experiments relating to accuracy were carried out, yielding the same result: namely, that the new iodine-free reagents containing triiodide were more accurate. This is a very desirable feature which can, for example, provide increased efficiency in a manufacturing process where the degree of accuracy is critical.

In these improved, iodine-free reagents, a range of triiodide of 0.03–0.7 mole per liter is useful. However, the preferred range of triiodide is 0.05–0.6 moles per liter. In order to convert substantially all of the iodine into triiodide during formulation of the reagent in accordance with equation (2), the water that is present prior to adding iodine should be present in an amount at least ⅓ of the amount of iodine on a molar basis.

These new reagents can be employed in kits that are sold to users for the determination of water content. An example is a sealed vial containing these new reagents, where the unknown sample can be introduced into the vial (as by breaking a seal), in the manner taught by U.S. Pat. No. 5,179,024.

While this invention has been described with respect to particular embodiments concerning novel methods for making iodine-free reagents, it will be apparent to those of skill in the art that variations may be made therein without departing from the spirit and scope of the present invention. These inventive processes require only small amounts of iodine and provide reagents having good titer strength and reproducible properties when analyzed on a batch-to-batch basis during multiple production runs.

The scope of this invention is intended to be limited only by the issued claims thereof.

I claim:

1. A method for preparing a one-component iodine-free volumetric Karl Fischer reagent suitable for determining the water content of a sample using the Karl Fischer reaction in which water reacts with an oxidizing agent on a quantitative basis, said reagent containing an amine, $SO_2$ and triiodide as the oxidizing agent and having a final amine/$SO_2$ ratio, including the sequential steps of:

preparing a first solution containing a solvent and a mixture of amine and $SO_2$ having a first amine/$SO_2$ ratio outside the range 0.6/1–1.2/1, said amine being selected from the group consisting essentially of primary and secondary acyclic amines, adding iodine to said solution, converting iodine in said solution to triiodide to produce an iodine-free solution, and adjusting the relative amounts of amine and $SO_2$ in said iodine-free solution to establish a final solution having a final amine/$SO_2$ ratio within the range of about 0.4/1–1.5/1, thereby producing said Karl Fischer reagent in which the molar amount of $SO_2$ in said reagent is greater than the molar amount of triiodide in said reagent.

2. The method of claim 1, where said amine is diethanolamine.

3. The method of claim 1, where said converting step is accomplished by adding water to said first solution containing iodine, amine and $SO_2$.

4. The method of claim 1, where said adjusting step is accomplished by adding amine and/or $SO_2$ to said iodine-free solution.

5. The method of claim 1, where said reagent contains iodine in an amount less than 1% of the amount of triiodide in said reagent.

6. The method of claim 1, where the amount of triiodide in said reagent is in the range of about 0.05–0.6 moles per liter.

7. The method of claim 6, wherein said reagent contains iodine in an amount less than $10^{-2}$ moles per liter.

8. The method of claim 1, including the further step of using said one-component Karl Fischer reagent to determine the water content of a sample by a volumetric Karl Fischer analysis wherein water to be determined reacts with said triiodide on a quantitative basis, the amount of reacted triiodide being a measure of the amount of water present in said sample.

9. A method for making a one-component iodine-free volumetric Karl Fischer reagent suitable for determining the water content of a sample using the Karl Fischer reaction in which water reacts with an oxidizing agent on a quantitative basis, said reagent containing an amine, $SO_2$ and triiodide as an oxidizing reagent and having a final amine/$SO_2$ ratio, including the steps of:

preparing a first solution containing a solvent and a mixture of amine and $SO_2$ having a first amine/$SO_2$ ratio outside the range 0.4/1–8/1, said amine being chosen from the group consisting essentially of imidazole and its derivatives, adding iodine to said solution, converting iodine in said solution to triiodide to produce an iodine-free solution, and adjusting the relative amounts of amine and $SO_2$ in said iodine-free solution to establish a final solution having said final amine/$SO_2$ ratio within the range of about 0.3/1–12/1, thereby producing said Karl Fischer reagent in which the molar amount of $SO_2$ in said reagent is greater than the molar amount of triiodide in said reagent.

10. The method of claim 9, where said converting step includes adding water to said first solution containing iodine, amine and $SO_2$.

11. The method of claim 9, where said adjusting step includes adding amine and/or $SO_2$ to said iodine-free solution.

12. The method of claim 9, where said reagent additionally contains iodine in an amount less than 1% of the amount of triiodide ions in said reagent.

13. The method of claim 9, where said triiodide is present in said reagent in the range of about 0.05–0.6 moles per liter.

14. The method of claim 13, where said reagent additionally contains iodine in an amount less than $10^{-2}$ moles per liter.

15. The method of claim 9, including the further step of using said one-component Karl Fischer reagent to determine the water content of a sample by a volumetric Karl Fischer analysis wherein water to be determined reacts with said triiodide on a quantitative basis, the amount of reacted triiodide being a measure of the amount of water present in said sample.

16. A method for preparing a one-component iodine-free volumetric Karl Fischer reagent suitable for determining the water content of a sample using the Karl Fischer reaction in which water reacts with an oxidizing agent on a quantitative basis, said reagent containing an amine, $SO_2$ and triiodide as an oxidizing agent and having a final amine/$SO_2$ ratio, said method including the steps of:

forming an iodine-free triiodide solution, said triiodide being present in an amount between about 0.05 moles per liter and 0.6 moles per liter, establishing a first amine/$SO_2$ ratio in said solution, and establishing a final amine/$SO_2$ ratio in said solution which is different than said first amine/$SO_2$ ratio to produce a one-component iodine-free Karl Fischer reagent in which the molar amount of $SO_2$ is greater than the molar amount of triiodide.

17. The method of claim 16, where said amine is selected from the group consisting essentially of imidazole and its derivatives.

18. The method of claim 17, where said final amine/$SO_2$ ratio is in the range 0.3/1–12/1.

19. The method of claim 16, where said amine is selected from the group consisting of primary and secondary acyclic amines.

20. The method of claim 19, where said final amine/$SO_2$ ratio is in the range 0.4/1–1.5/1.

21. A method for making an iodine-free single component Karl Fisher reagent suitable for determining the water content of a sample using the Karl Fischer reaction in which water reacts with an oxidizing agent on a quantitative basis, said reagent containing amine, $SO_2$ and triiodide as the oxidizing agent and having a final amine/$SO_2$ ratio, including the steps of:

dissolving $SO_2$ and amine in a first solution, the ratio of amine/$SO_2$ being different than said Final amine/$SO_2$ ratio, adding an amount of iodine to said first solution and thereafter performing the consecutive steps of first converting a portion of said iodine to iodide, second converting the balance of said iodine to triiodide to produce an iodine-free second solution having a concentration of triiodide in the range of about 0.05–0.6 moles per liter, and obtaining said final amine/$SO_2$ ratio in said second solution to produce said iodine-free Karl Fischer reagent having a molar amount of $SO_2$ therein which is greater than the molar amount of triiodide therein.

22. The method of claim 21, where said reagent contains iodine in an amount less than 1% of the amount of triiodide present in said reagent.

23. The method of claim 21, where said first converting step includes adding water to said first solution.

24. The method of claim 23, where said second converting step includes reacting iodine with iodide.

25. A method for making a one-component iodine-free volumetric Karl Fischer reagent suitable for determining the water content of a sample using the Karl Fischer reaction in which water reacts with an oxidizing agent on a quantitative basis, said reagent including the steps of:

dissolving $SO_2$ and amine in a solvent to produce a first solution having water therein, said amine and $SO_2$ being in said solution in a first amine/$SO_2$ ratio, adding a solid iodine source to said solution to produce iodide ions and to deplete all of said water in said solution, and converting further amounts of iodine from said solid iodine source to triiodide in the amount 0.05–0.6 moles per liter to produce said Karl Fischer reagent having a molar amount of $SO_2$ therein that is greater than the molar amount of triiodide therein and having a second amine/$SO_2$ ratio that is different than said first amine/$SO_2$ ratio.

26. A method for making a one-component iodine-free volumetric Karl Fischer reagent suitable for determining the water content of a sample using the Karl Fischer reaction in which water reacts with an oxidizing agent on a quantitative basis, said reagent having triiodide as tile oxidizing agent, said method including the steps of:

preparing a first solution having an amine, $SO_2$ and iodine therein, said amine and $SO_2$ being present in a first amine/$SO_2$ ratio, converting said first solution to an iodine-free second solution having triiodide therein in an amount between about 0.05–0.6 moles per liter and having a second amine/$SO_2$ ratio that is different than said first amine/$SO_2$ ratio, the molar amount of $SO_2$ in said second solution being greater than the molar amount of triiodide therein.

27. The method of claim 26, where said converting step is done by adding water to said first solution.

28. The method of claim 26, where said converting step is done by exposing said first solution to a temperature in excess of about 40° C. for a time period sufficient to produce said iodine-free second solution containing triiodide as an oxidizing species.

* * * * *